US00PP23042P3

(12) United States Plant Patent
Chandler

(10) Patent No.: US PP23,042 P3
(45) Date of Patent: Sep. 18, 2012

(54) STRAWBERRY PLANT NAMED 'FL 05-107'

(50) Latin Name: ***Fragaria×ananassa* Duchesne**
Varietal Denomination: FL 05-107

(75) Inventor: Craig K. Chandler, Tampa, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/930,400

(22) Filed: Jan. 6, 2011

(65) Prior Publication Data

US 2012/0180172 P1 Jul. 12, 2012

(51) Int. Cl.
*A01H 5/00* (2006.01)

(52) U.S. Cl. ..... Plt./208

(58) Field of Classification Search ..... Plt./208, Plt./209

See application file for complete search history.

*Primary Examiner* — Kent L Bell

(74) *Attorney, Agent, or Firm* — Jondle & Associates, P.C.

(57) ABSTRACT

A new and distinct variety of strawberry (*Fragaria×ananassa*), which originated from seed produced by a hand-pollinated cross between 'Florida Radiance' and 'Earlibrite'. The new strawberry, named 'FL 05-107', is distinguished by its ability to produce fruit that are exceptionally uniform, in terms of shape, size, and color when grown in west central Florida or other areas that have a subtropical climate similar to that of west central Florida.

1 Drawing Sheet

Botanical designation: *Fragaria×ananassa* Duchesne.

BACKGROUND OF THE NEW VARIETY

The present invention relates to a new and distinct variety of strawberry (*Fragaria×ananassa* Duchesne) plant named 'FL 05-107' and more particularly to a strawberry plant that is distinguished by its ability to produce fruit that are exceptionally uniform, in terms of shape, size, and color, during the winter in west central Florida. Asexual propagation was performed at Balm, Fla. where the selection was made and plants were tested. Contrast is made to 'Strawberry Festival' (U.S. Plant Pat. No. 14,739) and 'Florida Radiance' (U.S. Plant Pat. No. 20,363), currently the dominant varieties in Hillsborough County, Fla., for reliable description. This new variety is a promising candidate for commercial success because it produces large, attractive, and easy-to-harvest fruit that are firm and flavorful during a desirable market window.

ORIGIN OF THE VARIETY

This strawberry plant (genotype) originated in a strawberry breeding plot at Balm, Fla. The seed parent was 'Florida Radiance', a strawberry variety with high early-season yield potential and the ability to produce large, glossy fruit throughout the main production period. The pollen parent was 'Earlibrite' (U.S. Plant Pat. No. 13,061), a strawberry variety with a compact plant habit and the ability to produce large, bright-red fruit. The seeds resulting from the controlled hybridization were germinated in a greenhouse and the resulting seedlings were planted and allowed to produce daughter plants by asexual propagation (i.e. by runners). Two daughter plants from each seedling were transplanted to raised beds, where they fruited. 'FL 05-107' strawberry (as represented by two daughter plants from the original seedling) exhibited attractive fruit, and therefore was selected for further evaluation. 'FL 05-107' was the $107^{th}$ selection numbered in the 2005-2006 stage 1 trial, and thus was designated 'FL 05-107'.

'FL 05-107' has been asexually propagated in Balm, Fla. by runners, annually, and further test plantings have established that the vegetative and fruit characteristics of the propagules are identical to the initial two daughter plants.

SUMMARY OF THE VARIETY

'FL 05-107', when grown in a subtropical fall and winter climate, is set apart from all other strawberry plants known by the inventor by a combination of the following characteristics: compact, upright growth habit; ease of harvest; low percentage of misshapen fruit; and relatively steady yield of fruit that are consistently attractive, firm, abrasion-resistant, and pleasantly sweet.

BRIEF DESCRIPTION OF THE PHOTOGRAPHS

The accompanying photographs show a typical specimen of a 5-month-old plant and ripe fruit as seen in March 2010 in west central Florida.

DETAILED BOTANICAL DESCRIPTION

Figure 1:
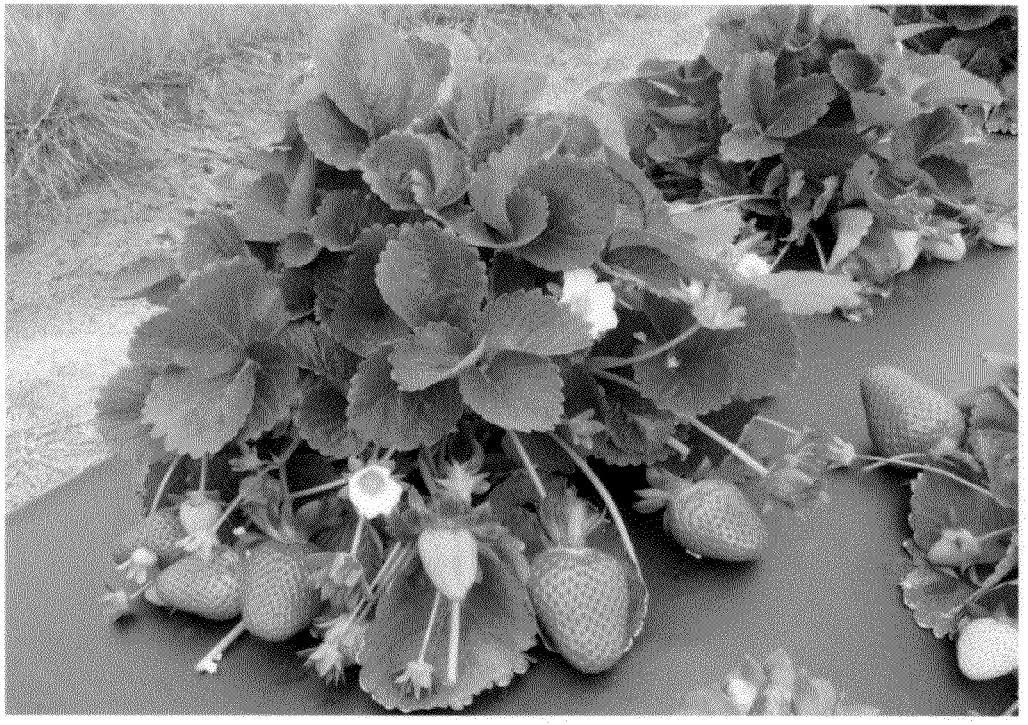
FIG. 1 shows a whole plant, including leaves, buds and inflorescence.
Figure 2:
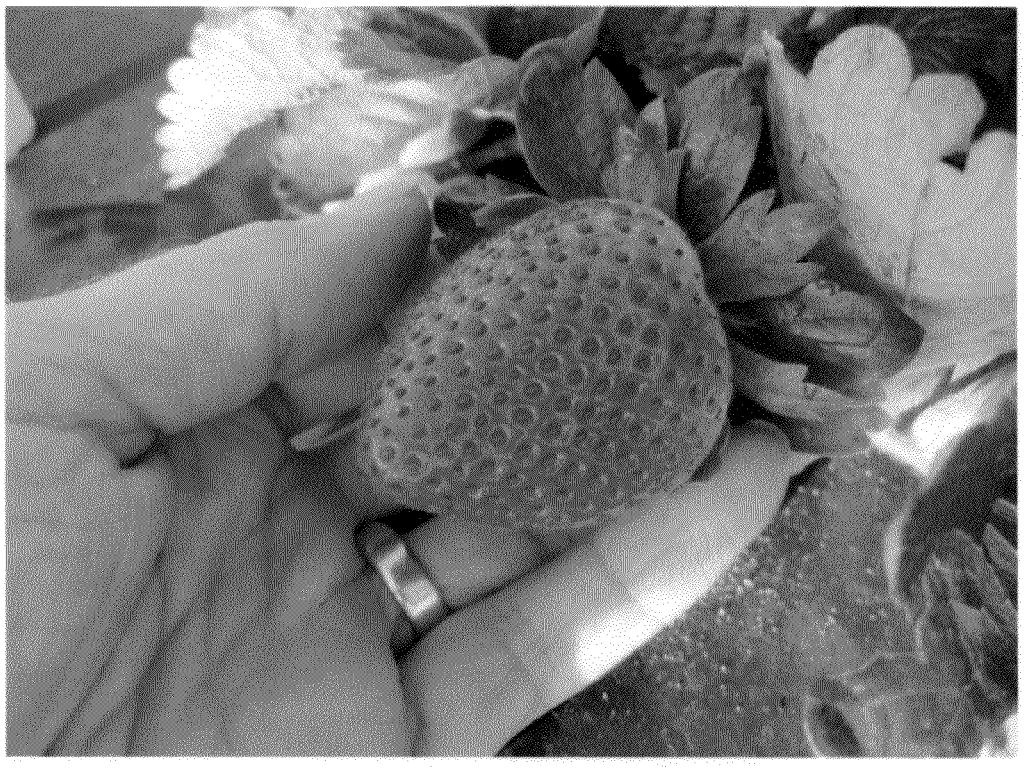
FIG. 2 is a up-close of the fruit.

The following botanical description is that of 6-month-old mature plants of the variety grown under the ecological conditions (warm days, cool nights) prevailing at Balm, Fla. in March. Colors are described using a standard Royal Horticultural Society (R.H.S.) Colour Chart 1995 Edition.

'FL 05-107' is a short day variety. Average height and width for mature plants is 22 cm and 28 cm respectively. Average petiole length and diameter is 16.0 cm and 3.5 mm respectively, and the petioles have a light to medium pubescence. Average length and breadth of terminal leaflets is 74 mm and 65 mm respectively. Average length and breadth of secondary leaflets is 65 mm and 60 mm respectively. Number of leaflets per leaf is 3, and leaflet shape is orbiculate. Leaflet apex and base are obtuse. Leaflet margins are crenate and average 22 serrations per terminal leaflet, and 17 per secondary leaflet. Leaflet upper surface texture is puberulous, and leaflet lower surface texture is scabrous. The upper leaf surface is a dark grey green (RHS 139B); the lower leaf surface is a light grey green (RHS 139C); and the petiole is a medium yellow green (RHS 145A). Leaf length including petiole is 27 cm, and leaf width is 13.5 cm. Petiolule length is 10 mm for the terminal leaflets and 5 mm for the secondary leaflets. Petiolule diameter is 2 mm for both terminal and secondary leaflets. Petiolule color is medium yellow green (RHS 145A). Stipule length is 35 mm and stipule width is 18 mm. Stipule color is medium yellow green (RHS 145A).

Flower bud shape is campanulate, and the color is medium yellow green (RHS 145A). Bud length and width are 15 mm. Petal shape is round with a base and apex that are obtuse. Petal margins are entire, and both petal surfaces are solid white (RHS 155C). Flowers open at or below canopy height, and have 6 to 8 petals and an average of 27 stamens. Stamen length is 3 mm. Anther shape is oval, length is 1 mm, width is less than 1 mm, and the color is yellow (RHS 12B). Pollen amount is abundant and color is yellow (RHS 15B). Stigma shape is round and the color is medium yellow green (RHS 145A). Style length is less than 1 mm and the color is medium yellow green (RHS 145A). Ovary length is less than 1 mm and the color is medium yellow green (RHS 145A). Individual petals have a length of 11 mm and a width of 10 mm. The mean diameter of the corolla (i.e. the petals collectively) is 30 mm, and the depth is 4 mm. The upper surface color of the calyx is light grey green (RHS 139C). The lower surface color of the calyx is yellow green (RHS 141B). The number of sepals is 10, sepal length is 17 mm, and width is 7 mm. Sepal shape is elliptic with an apex that is mucronulate and margins that are entire. The sepal color on the upper surface is light grey green (RHS 139C) and the lower surface is yellow green (RHS 141B). Pedicels attached to mature primary fruit are 11.7 to 14.4 cm long, 2 mm in diameter, and a color of medium yellow green (RHS 145A). Branching of the inflorescence usually occurs very close to the crown. At peak production, the plant will have four crowns, each producing a truss, and each truss will have three to seven pedicels. Fruiting truss length is 15 cm, truss diameter is 10 cm, and truss color is medium yellow green (RHS 145A). Mean fruit weight is greater than or equal to that of 'Strawberry Festival' and less than or equal to that of 'Florida Radiance' (Tables 1 and 2). Fruit are mostly medium conical in shape, with primary fruit weighing 30-40 g and secondary and tertiary fruit weighing 10-30 g. Fruit length is 54 mm and width is 42 mm. Occasionally, a primary fruit of 'FL 05-107' will have a small hollow cavity at its center with a length of 24 mm and a width of 12 mm. A cavity in a secondary or tertiary fruit of this variety is rarely, if ever, seen. The achenes are slightly sunken, giving the fruit a smooth appearance. The number of achenes per berry is 230 with a color of yellow-gold (RHS 14B). External fruit color is a glossy bright red (RHS 34B) and not significantly different than that of 'Florida Radiance' fruit (Table 3). The internal color of 'FL 05-107' fruit is light orange (RHS 32C), however, significantly less red than that of 'Florida Radiance' and 'Strawberry Festival' fruit (Table 3). The calyx is generally medium to large and attractive. Fruit of 'FL 05-107' are very firm and are firmer and have skin that is as resistant as or more resistant to abrasion than that of 'Florida Radiance' and 'Strawberry Festival' fruit (Table 3). The flavor of 'FL 05-107' fruit is low-acid and sweet and considered to be as good as 'Strawberry Festival' and better than 'Florida Radiance' fruit. The preferred planting period for 'FL 05-107' is October 1$^{st}$ to October 15$^{th}$. Yields of 'FL 05-107' were greater than those of 'Strawberry Festival' during both the 2008-2009 and 2009-2010 seasons (Tables 1 and 2), but were less than 'Florida Radiance' during the 2009-2010 season (Table 2). 'FL 05-107' is less resistant to cracking of the fruit by rain and sprinkler irrigation (used for freeze protection) than 'Strawberry Festival' and 'Florida Radiance'. Also, 'FL 05-107' may be more susceptible to Botrytis fruit rot (caused by *Botrytis cinerea*) than 'Strawberry Festival' and 'Florida Radiance'. 'FL 05-107' does appear to have some resistance to anthracnose fruit rot (caused by *Colletotrichum acutatum*). 'FL 05-107' is non-everbearing.

'FL 05-107' produces many runners which develop into sturdy, compact daughter plants. This is in contrast to 'Florida Radiance', whose daughter plants have weak petioles that are susceptible to breakage during digging and handling.

TABLE 1

Performance of two strawberry genotypes at Balm, Florida during the 2008-2009 season.
Marketable yield (g/plant)

| Variety | December | January | February | March | Total | Wt/fruit[z](g) |
|---|---|---|---|---|---|---|
| 'FL 05-107' | 3 a[y] | 167 a | 417 a | 465 a | 1060 a | 22.4 a |
| 'S. Festival' | 10 a | 124 b | 163 b | 316 b | 613 b | 19.4 b |

[z]Mean fruit weight was determined by dividing total marketable fruit yield per plot by total marketable fruit number per plot.
[y]Means based on four replications of 10 plants each. Mean separation within columns by LSD test, $P < 0.05$.

TABLE 2

Performance of three strawberry genotypes at Balm, Florida and Dover, Florida during the 2009-2010 season.
Marketable yield (g/plant)

| Variety | December | January | February | March | Total | Wt/fruit[z](g) |
|---|---|---|---|---|---|---|
| GCREC | | | | | | |
| 'FL 05-107' | 72 a | 107 ab | 128 b | 425 b | 732 b | 25.7 b |
| 'F. Radiance' | 72 a[y] | 86 b | 210 a | 558 a | 925 a | 28.5 a |
| 'S. Festival' | 47 a | 120 a | 86 b | 417 b | 670 b | 24.1 b |
| Dover | | | | | | |
| 'FL 05-107' | 29 a | 46 b | 83 a | 295 a | 453 b | 25.5 a |
| 'F. Radiance' | 19 ab | 80 a | 90 a | 480 a | 670 a | 26.7 a |
| 'S. Festival' | 5 b | 61 b | 22 b | 278 a | 366 b | 22.4 a |

[z]Mean fruit weight was determined by dividing total marketable fruit yield per plot by total marketable fruit number per plot.
[y]Means based on four replications of 10 plants each. Mean separation within columns by LSD test, $P < 0.05$.

TABLE 3

Postharvest analysis of three strawberry genotypes grown at Balm, Florida and Dover, Florida.

| Cultivar | Ext. Color[z] | Int. Color[y] | Gloss[x] | Firmness[w] | Skin Toughness[v] |
|---|---|---|---|---|---|
| GCREC | | | | | |
| 'FL 05-107' | — | — | 3.1 a | 4.0 a | 3.9 a |
| 'F. Radiance' | — | — | 3.4 a[u] | 3.1 b | 3.1 c |
| 'S. Festival' | — | — | 3.0 a | 2.9 b | 3.5 b |

TABLE 3-continued

Postharvest analysis of three strawberry genotypes grown at Balm, Florida and Dover, Florida.

| Cultivar | Ext. Color[z] | Int. Color[y] | Gloss[x] | Firmness[w] | Skin Toughness[v] |
|---|---|---|---|---|---|
| | | | Dover | | |
| 'FL 05-107' | 38.9 a | 12.6 b | 3.0 a | 3.8 a | 4.0 a |
| 'F. Radiance' | 38.9 a | 23.2 a | 3.1 a | 2.9 b | 3.0 b |
| 'S. Festival' | 31.7 b | 26.4 a | 3.3 a | 2.6 b | 3.6 a |

Color ratings were performed on Mar. 9, 2010; gloss, firmness, and skin toughness ratings were performed on Apr. 2, 2010.

[z]mean a-value from colorimeter readings after 1 day of storage at 5° C.

[y]mean a-value from colorimeter readings after 1 day of storage at 5° C.

[x]1-5 visual ratings under fluorescent lighting; 5 = high external gloss; 1 = no gloss

[w]1-5 scale by pressing between thumb and index finger; 5 = high firmness; 1 = soft TABLE 3-continued Postharvest analysis of three strawberry genotypes grown at Balm, Florida and Dover, Florida.

| Cultivar | Ext. Color[z] | Int. Color[y] | Gloss[x] | Firmness[w] | Skin Toughness[v] |
|---|---|---|---|---|---|

[v]1-5 scale by abrading with thumb; 5 = high resistance to abrasion; 1 = no resistance to abrasion

[u]Means based on four replications. Mean separation within columns by LSD test, $P < 0.05$.

I claim:

1. A new and distinct strawberry plant as illustrated and described, characterized by 1) a compact, upright growth habit, 2) a lack of misshapen fruit; and 3) a steady yield of medium to large fruit that are attractive, firm, abrasion resistant, and pleasantly sweet when grown in west central Florida.

* * * * *